United States Patent [19]

Stokes et al.

[11] Patent Number: 4,920,807
[45] Date of Patent: May 1, 1990

[54] METHOD FOR PREDICTING THE FATIGUE LIFE OF A VEHICLE SUSPENSION COMPONENT

[75] Inventors: Richard S. Stokes, Orwigsburg; Robert M. Muldowney, Stowe, both of Pa.

[73] Assignee: Dana Corporation, Toledo, Ohio

[21] Appl. No.: 350,594

[22] Filed: May 11, 1989

[51] Int. Cl.$^5$ ............................................. G01N 3/32
[52] U.S. Cl. ..................................................... 73/808
[58] Field of Search .................................. 73/808–815

[56] References Cited

PUBLICATIONS

SAE Technical Paper No. 680084, Lipson et al., (1968).
SAE Technical Paper No. 861849, Kececioglu et al., (1986).

Primary Examiner—Robert R. Raevis
Attorney, Agent, or Firm—MacMillan, Sobanski & Todd

[57] ABSTRACT

A method for obtaining fatigue life information for an article is disclosed. Initially, an area of interest is determined on the article. A durability schedule is defined for that article as a predetermined number of passes through each of a predetermined number of events, each of the events being defined by the generation of strains in the article having a predetermined range of magnitudes and frequencies. A total effective damage factor caused to the component by one pass through each of the events is next determined, which permits the determination of a total durability factor for all of passes for all of the events defined in the durability schedule. The article is then tested by subjecting it a plurality of passes through all of the events defined in the durability schedule until a termination criteria is reached. Then, a total actual damage factor can be determined based upon the number of tested passes through each of the events defined in the durability schedule. A final durability factor for the article is lastly determined by dividing the total actual damage factor by the total durability factor. A plurality of final durability factors can be used to obtain the desired fatigue life information.

9 Claims, No Drawings

1

METHOD FOR PREDICTING THE FATIGUE LIFE OF A VEHICLE SUSPENSION COMPONENT

BACKGROUND OF THE INVENTION

This invention relates in general to fatigue life estimation procedures and in particular to a method for obtaining fatigue life prediction information for a vehicle suspension component or similar article which is subjected to laboratory durability testing using real time loading.

Throughout the course of designing a new product, various testing and analysis procedures are often employed to determine the suitability of the product for its intended use. For convenience, the testing procedures are usually performed in a laboratory in such a manner as to closely simulate the service environment of the product. The nature and quantity of the testing procedures will, therefore, vary according to the nature of the product and its intended life span. For example, when the product is a vehicle suspension component, real time road simulation testing is usually performed. Such real time road simulation testing typically involves subjecting the suspension component to a series of loadings by means of a test device. The test loadings follow the magnitude and frequency content of the loadings which are expected to be received in the normal service environment of the vehicle.

Once testing has been performed on a particular product, the results thereof are analyzed so as to generate statistical inferences regarding the service life of the product. A known statistical procedure which has been used in the past to predict fatigue life is the Weibull analysis method. The Weibull analysis method requires that several samples of the product be subjected to identical testing procedures until some predetermined test termination criteria is met. The data which is acquired from each of those testing procedures is used in the Weibull analysis method to estimate the fatigue life of the product.

Unfortunately, the Weibull analysis method assumes that the amplitudes of the loadings applied to each of the tested samples of the product are constant over a period of time. This assumption is inconsistent with the actual use of many products, including vehicle suspension components, which are subjected to widely varying amplitude loadings during use. Thus, the Weibull analysis method has not been well suited for use in connection with real time road simulation testing and the data generated thereby to predict the fatigue life of vehicle suspension components.

SUMMARY OF THE INVENTION

This invention provides a method whereby data generated from real time variable amplitude loading on an article can be used in conjunction with the Weibull analysis method to obtain fatigue life prediction information. Initially, an area of interest is determined on the article. A durability schedule is defined for that article as a predetermined number of passes through each of a predetermined number of events, each of the events being defined by the generation of strains in the article having a predetermined range of magnitudes and frequencies. A total effective damage factor caused to the component by one pass through each of the events is next determined, which permits the determination of a total durability factor for all of passes for all of the events defined in the durability schedule. The article is then tested by subjecting it a plurality of passes through all of the events defined in the durability schedule until a termination criteria is reached. Then, a total actual damage factor ca be determined based upon the number of tested passes through each of the events defined in the durability schedule. A final durability factor for the article is lastly determined by dividing the the total actual damage factor by the total durability factor. A plurality of final durability factors can be used to obtain the desired fatigue life information.

It is an object of this invention to provide a method for obtaining fatigue life prediction information concerning a vehicle suspension component which is subjected to laboratory durability testing using real time variable amplitude loading.

Other objects and advantages of the invention will become apparent to those skilled in the art from the following detailed description of the preferred embodiment.

DETAILED DESCRIPTION OF THE PREFERRED EMBODIMENT

The first step in the method of this invention is to determine the primary failure mode or other area of design concern of the article, which may be a vehicle suspension component. This initial determination is performed so that the scope of the subsequent test data acquisition, which will be explained in detail below, can be limited to that particular area of concern. To accomplish this initial determination, any one of the various known methods of full field stress analysis may be used. Alternatively, reference may be made to previous test information concerning the component. In any case, the area of the component which is first subject to failure, or which is otherwise of concern, is initially identified.

Once the area of concern of the component has been identified, a plurality of conventional strain gauges are attached to the component at that area. As is well known, the strain gauges generate electrical signals which are representative of the magnitude of the strains present in the areas of the component at which they are attached. As will be explained in greater detail below, the strain gauges measure elongations which are induced in the component during the testing process so as to permit an analysis of whether the component design meets established fatigue criteria.

Following the attachment of the strain gauges, the component is installed on a conventional laboratory test device. The test device is adapted to apply strains of varying magnitude and frequency to the component. The specific magnitudes and frequencies of such strains are predetermined, based upon the nature of the component and its intended use. A durability schedule is used to define which of the predetermined magnitudes and frequencies of the strains the component must endure without failure to be acceptable. Thus, the durability schedule defines the magnitudes and frequencies of the strains which will be applied to a particular component by the test device.

The durability schedule defines the testing criteria for a given article as consisting of a predetermined number of passes through each of a predetermined number of events. Each event is defined as the generation of strains in the article having a predetermined range of magnitudes and frequencies. For the purposes of illustration, let it be assumed that a durability schedule for a particular vehicle suspension component is defined by five different events, referred to as Event Nos. 1 through 5. Event No. 1 is characterized by the generation of strains in the component within a first predetermined range of magnitudes and frequencies, while the other events are characterized by strains at other predetermined ranges of magnitudes and frequencies. Let it further be assumed that the durability schedule defines that each of the events must be repeated the number of times shown in Table 1.

TABLE 1

| Event Number | Required Passes |
|---|---|
| 1 | 1000 |
| 2 | 500 |
| 3 | 2200 |
| 4 | 4400 |
| 5 | 5600 |

Thus, in order to satisfy this particular durability schedule, the suspension component must be able to withstand all of the required passes through each of the five events without failing.

Having defined the testing criteria for the component by means of the durability schedule, the next step in the method involves the determination of a total effective damage factor related to one pass through each of the events defined in the durability schedule. This determination is preferably made by subjecting the component to a single pass through each of Event Nos. 1 through 5 and measuring the resultant strains induced in the component. As mentioned above, the test device induces the strains in the component, causing elongations thereof. The strain gauges are responsive to these elongations for generating electrical signals which are proportional to the induced strains. Preferably, a computer is used to selectively interrogate each of the strain gauges and store the raw data generated thereby. For convenience, the component may be subjected to one pass of each of the five events sequentially, thereby permitting all of the strain measurements for the five events to be made during the same preliminary testing period. However, as will become apparent below, each event may be performed individually (and the corresponding total effective damage factor related to that one event may be determined) before proceeding to the next event if desired.

Once the raw strain data has been gathered for the single pass through the event, Event No. 1 for example, it is transformed into a tabulation of peak-valley counts using a well known rainflow counting algorithm. The following table illustrates a typical tabular listing of the number of cycles at each of a plurality of strain levels obtained from rainflow counted data for Event No. 1.

TABLE 2

| Strain (micro strain) | Cycles At Strain Level |
|---|---|
| 4000 | 1 |
| 2667 | 2 |
| 2000 | 5 |
| 1667 | 10 |
| 1333 | 15 |
| 1000 | 25 |
| 667 | 140 |
| 333 | 250 |

For each of the strain levels shown in Table 2, it is next necessary to determine the number of cycles to failure using appropriate parameters. The number of cycles to failure at each strain level can be calculated from the following equation, obtained from the 1988 SAE Handbook—Part 1 (page 3.71).

$$e/2 = (o/E)(2N)^b + x(2N)^c$$

wherein:
e/2 = true strain amplitude
o = fatigue strength coefficient
E = modulus of elasticity
N = number of cycles to failure
b = fatigue strength exponent
x = fatigue ductility coefficient
c = fatigue ductility exponent The parameters are determined by the material used to form the component being tested. If, for example, the material used to form the component is SAE 1005 steel, the following parameters for the strain level of 4000 micro strain:

$e/2 = 4000 \times 10E(-6)$
$o = 84000$
$E = 30E(6)$
$b = -0.09$
$x = 0.15$
$c = -0.43$ Using these parameters, N = 5312 cycles to failure at the micro strain level. The number of cycles to failure can be calculated in a similar manner for each of the other strain levels for Event No. 1, as shown in Table 3.

By dividing the number of cycles at each strain level by the corresponding number of cycles to failure at that strain level, an effective damage factor is calculated. The effective damage factors represent the relative amount of damage caused to the component at each of the strain levels during Event No. 1. Table 3 illustrates these calculations.

TABLE 3

| Strain (micro strain) | Cycles At Strain Level | Cycles To Failure | Effective Dam. Factor |
|---|---|---|---|
| 4000 | 1 | 5312 | 1.882E(−4) |
| 2667 | 2 | 19667 | 1.017E(−4) |
| 2000 | 5 | 55442 | 9.018E(−5) |
| 1667 | 10 | 114195 | 8.757E(−5) |
| 1333 | 15 | 303813 | 4.937E(−5) |
| 1000 | 25 | 1319180 | 1.895E(−5) |
| 667 | 140 | 18561400 | 7.542E(−6) |
| 333 | 250 | 1.1128E(10) | 2.247E(−8) |

By summing the effective damage factors at each of the strain levels, a total effective damage factor can be calculated for one pass through Event No. 1. Using the figures shown in Table 3, the total effective damage for Event No. 1 is 5.435E(−4). The above steps are then repeated for Event Nos. 2 through 5 defined in the durability schedule for the component. Accordingly, a total effective damage factor is calculated for a single pass through each of Event Nos. 1 through 5.

Having determined a total effective damage factor for each of the Event Nos. 1 through 5, it is next desirable to determine a total durability factor for the entire durability schedule. To do this, the event having the highest total effective damage is initially assigned a relative damage factor of 1.00. The remaining events are assigned relative damage factors which are less than 1.00 by dividing them by the highest total effective damage factor. As a result, each event in the durability schedule has a relative damage factor assigned to it.

Next, a durability factor is determined for each of the events. The durability factors are calculated by multiplying required number of passes through each event (as defined in the durability schedule) by the corresponding relative damage factor (as determined above). Table 4 illustrates these calculations.

TABLE 4

| Event Number | Required Passes | Total Effective Damage Factors | Rel. Dam. Factors | Durability Factors |
|---|---|---|---|---|
| 1 | 1000 | 5.435E(−4) | 1.000 | 1000.00 |
| 2 | 500 | 2.761E(−4) | 0.508 | 254.00 |
| 3 | 2200 | 4.691E(−5) | 0.086 | 189.20 |
| 4 | 4400 | 1.972E(−5) | 0.036 | 158.40 |
| 5 | 15900 | 2.567E(−6) | 0.005 | 79.50 |

By totaling the durability factors calculated for each of the events, a total durability factor is generated. Using the figures shown in Table 4, the total durability factor for the entire durability schedule is equal to 1681.10. This figure represents the relative amount of damage caused to the component by subjecting it to all of the required passes of each of the events defined in the durability schedule.

At this point, the component can be tested in a conventional manner by the test device. To do this, the test device subjects the component to repeated passes through each of the events defined in the durability schedule. This testing continues until it is terminated because of failure of the component or until it is suspended for some other reason. When the testing is concluded, the number of passes through each event will preferably meet or exceed the required number of passes defined in the durability schedule.

In any case, when the testing of the component is concluded, a total actual damage factor for that tested component is determined. This total actual damage factor is calculated by initially multiplying the number of actual passes through each of the events during the testing process by the respective relative damage factors assigned to those events, as previously determined. Table 5 illustrates these initial calculations.

TABLE 5

| Event Number | Actual Test Passes | Relative Dam. Factors | Actual Dam. Factors |
|---|---|---|---|
| 1 | 1500 | 1.000 | 1500.00 |
| 2 | 800 | 0.508 | 406.04 |
| 3 | 3000 | 0.086 | 258.00 |
| 4 | 10000 | 0.036 | 360.00 |
| 5 | 13000 | 0.005 | 65.00 |

By totaling the actual damage factors for each of the events, a total actual damage factor is generated. Using the figures shown in Table 5, the total actual damage factor is equal to 2589.04. This figure represents the relative amount of the total actual damage caused to the component by subjecting it to repeated test passes through each of the events during the testing process.

Lastly, by dividing the total actual damage factor by the total durability factor, a final durability factor can be obtained. This final durability factor represents the amount by which the component exceeds (if the final durability factor is greater than 1.00) or falls below (if the final durability factor is less than 1.00) the requirements defined in the durability schedule. Using the numbers in the illustrated tables, the final durability factor of the tested component is equal to 1.54 (2589.04 divided by 1681.10). In other words, the predicted life of the tested component is 1.54 times greater than the requirements defined by the durability schedule.

By testing a plurality of samples of the component in the manner described above, a plurality of final durability factors can be generated. For example, assume that four samples of the component are tested, thereby yielding four different final durability factors shown in Table 6. By reference to conventional statistical tables, a median rank can be assigned to each of the final durability factors, as shown in Table 6.

TABLE 6

| Final Durability Factors | Median Rank |
|---|---|
| 1.33 | 15.91 |
| 1.34 | 38.57 |
| 1.38 | 61.43 |
| 1.54 | 84.09 |

These final durability factors can be easily plotted against the median ranks on conventional Weibull graph paper. The resultant graph can be used in a known manner to determine the desired fatigue life prediction information for the component. The Weibull analysis method is well known in the art of fatigue life prediction techniques.

In accordance with the provisions of the patent statutes, the principle and mode of operation of this invention have been explained in its preferred embodiment. However, it must be understood that the present invention may be practiced otherwise than as specifically explained and illustrated without departing from its spirit or scope.

What is claimed is:

1. A method for obtaining fatigue life information for an article comprising the steps of:
    (a) determining an area of interest on the article;
    (b) defining a durability schedule for the article as a predetermined number of passes through each of a predetermined number of events, each of the events being defined by the generation of strains in the article having a predetermined range of magnitudes and frequencies;
    (c) determining a total effective damage factor caused to the article by one pass through each of the events;
    (d) determining a total durability factor for all of passes for all of the events defined in the durability schedule;
    (e) testing the article by subjecting it to a plurality of passes through all of the events defined in the durability schedule until a termination criteria is reached;
    (f) determining a total actual damage factor based upon the number of tested passes through each of the events defined in the durability schedule;
    (g) determining a final durability factor for the article by dividing the the total actual damage factor by the total durability factor;
    (h) repeating steps (a) through (g) for a plurality of articles;
    (i) assigning a median rank to each of the final durability factors; and
    (j) obtaining the fatigue life information for an article based upon the final durability factors and the median ranks.

2. The method defined in claim 1 wherein said step (c) includes the steps of:
    (1) subjecting the article to a single pass through one of the events defined in the durability schedule;

(2) obtaining strain data from the area of interest of the article as a result of the event;

(3) determining the total effective damage caused to the component by the event; and (4) repeating steps (1) through (3) for each of the other events defined in the durability schedule.

3. The method defined in claim 2 wherein said step (3) includes the steps of:

(i) transforming the strain data into a tabulation of number of cycles at a plurality of strain levels;

(ii) determining the number of cycles to failure at each of the strain levels;

(iii) determining an effective damage factor at each of the strain levels;

(iv) summing the effective damage factors to determine a total effective damage factor for the event; and (v) repeating steps (i) through (iv) for each of the events.

4. The method defined in claim 1 wherein said step (d) includes the steps of:

(1) assigning a relative damage factor to each of the total effective damage factors;

(2) determining a durability factor of each of the events by multiplying the relative damage factor for that event by the predetermined number of passes through that event, as defined in the durability schedule; and (3) summing the durability factors to determine the total durability factor.

5. The method defined in claim 4 wherein said step (f) includes the steps of:

(1) multiplying the number of tested passes through each of the events by the relative damage factor for that event to determine an actual damage factor for each of the events; and (2) summing the actual damage factors to determine the total actual damage factor.

6. A method for obtaining fatigue life information for an article comprising the steps of:

(a) determining an area of interest on the article based upon the primary failure mode thereof;

(b) defining a durability schedule for the article as a predetermined number of passes through each of a predetermined number of events, each of the events being defined by the generation of strains in the article having a predetermined range of magnitudes and frequencies;

(c) subjecting the article to a single pass through one of the events defined in the durability schedule;

(d) obtaining strain data from the area of interest of the article as a result of the event;

(e) determining a total effective damage factor caused to the article by the event;

(f) repeating steps (c) through (e) for each of the other events defined in the durability schedule;

(g) assigning a relative damage factor to each of the total effective damages;

(h) determining a durability factor for each of the events defined in the durability schedule;

(i) determining a total durability factor for all of the events defined in the durability schedule;

(j) testing the article by subjecting it to a plurality of passes through all of the events defined in the durability schedule until a termination criteria is reached;

(k) determining an actual damage factor based upon the number of tested passes through each of the events;

(l) determining a total actual damage factor based upon the number of tested passes through each of the events defined in the durability schedule;

(m) determining a final durability factor for the article by dividing the the total actual damage factor by the total durability factor;

(n) repeating steps (a) through (m) for a plurality of articles;

(o) assigning a median rank to each of the final durability factors; and (p) obtaining the fatigue life information for an article based upon the final durability factors and the median ranks.

7. The method defined in claim 6 wherein said step (e) includes the steps of:

(1) transforming the strain data into a tabulation of number of cycles at a plurality of strain levels;

(2) determining the number of cycles to failure at each of the strain levels;

(3) determining an effective damage factor at each of the strain levels;

(4) summing the effective damage factors to determine a total effective damage factor for the event; and (5) repeating steps (1) through (4) for each of the events.

8. The method defined in claim 6 wherein said step (i) includes the steps of:

(1) assigning a relative damage factor to each of the total effective damage factors;

(2) determining a durability factor of each of the events by multiplying the relative damage factor for that event by the predetermined number of passes through that event, as defined in the durability schedule; and (3) summing the durability factors to determine the total durability factor.

9. The method defined in claim 8 wherein said step (1) includes the steps of:

(1) multiplying the number of tested passes through each of the events by the relative damage factor for that event to determine an actual damage factor for each of the events; and (2) summing the actual damage factors to determine the total actual damage factor.

* * * * *